United States Patent
Yamada et al.

(10) Patent No.: US 7,816,338 B2
(45) Date of Patent: Oct. 19, 2010

(54) COMPOSITIONS AND METHODS FOR INHIBITING CAR GENE EXPRESSION BY RNA INTERFERENCE

(75) Inventors: Tomoya Yamada, Osaka (JP); Yukihiro Hirose, Kyoto (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 12/183,354

(22) Filed: Jul. 31, 2008

(65) Prior Publication Data

US 2009/0053298 A1 Feb. 26, 2009

(30) Foreign Application Priority Data

Jul. 31, 2007 (JP) .............................. 2007-198725

(51) Int. Cl.
*A61K 31/70* (2006.01)
*C12Q 1/68* (2006.01)

(52) U.S. Cl. ............................................ 514/44; 435/6
(58) Field of Classification Search .................. 514/44; 435/6
See application file for complete search history.

(56) References Cited

U.S. PATENT DOCUMENTS

2004/0259247 A1* 12/2004 Tuschl et al. ................ 435/375
2006/0288436 A1* 12/2006 Moore et al. .................. 800/18

FOREIGN PATENT DOCUMENTS

WO 0225270 A1 3/2002
WO 2006064197 A2 6/2006

OTHER PUBLICATIONS

European Search Report for the related European Application No. 08252595.7 dated Dec. 1, 2008.
Chen et al.; "Human constitutive androstane receptor mediated methotrexate induction of human dehydroepiandrosterone sulfotransferase (hSULT2A1)"; Toxicology, vol. 231, No. 2-3; Feb. 24, 2007; available online Dec. 22, 2006; pp. 224-233.
Yamamoto, Yukio et al.; "The orphan nuclear receptor contitutive active/androstane receptor is essential for liver tumor promotion by phenobarbital in mice"; Cancer Resaerch, vol. 64, No. 20; Oct. 15, 2004; pp. 7197-7200.
Yang et al.; "A novel PNAi library based on partially randomized consensus sequences of nuclear receptors" Identifying the receptors involved in amyloid beta degradation; Genomics; vol. 88, No. 3; Aug. 23, 2006; available online May 2, 2006; pp. 282-292.
Swales, Karen et al.; "CAR, driving into the future"; Molecular Endocrinology; vol. 18, No. 7; Jul. 2004; pp. 1589-1598.
Yamada, Hideyuki et al.; "Induction of the hepatic cytochrome P4502B subfamily by xenobiotics: Research history, evolutionary aspect, relation to tumorigenesis, and mechanism"; Current Drug Metabolism; vol. 7, No. 4; May 2006; pp. 397-409.

* cited by examiner

*Primary Examiner*—J. E Angell
(74) *Attorney, Agent, or Firm*—Panitch Schwarze Belisario & Nadel LLP

(57) ABSTRACT

The present invention provides short interfering ribonucleic acid (siRNA), compositions and methods for inhibiting the CAR gene expression simply and rapidly, which can be used for evaluating toxicity of a chemical substance.

16 Claims, 3 Drawing Sheets

COMPOSITIONS AND METHODS FOR INHIBITING CAR GENE EXPRESSION BY RNA INTERFERENCE

BACKGROUND OF THE INVENTION

1. Field of the Invention

The present invention relates to inhibition by short interference RNA (hereinafter, referred to as siRNA in some cases) of expression of the nuclear receptor CAR that acts on transcriptional control of drug-metabolizing enzymes.

2. Description of the Related Art

Constitutive Active/Androstane Receptor (CAR) is a transcription factor belonging to the nuclear receptor family and plays a role of biological defense mechanism against is increase in drug level in a living body. In general, it is considered that CAR induces expression of drug-metabolizing enzymes in organs such as liver and enhances the metabolism of the drug to defend the body against the administered drug (Swales and Negishi, 2004, Mol. Endo. 18(7) 1589-1598).

On the other hand, it has been reported that such a defensive mechanism of CAR causes serious side effects in mice. For example, expression level of drug-metabolizing enzymes in the liver is increased by prolonged administration of phenobarbital, and further the increase in frequency of DNA replication and reduction in apoptosis via p53, i.e., tumor suppressor gene are observed. As a result, tumorigenic transformation of the liver is induced. It has been shown that the tumorigenic transformation mechanism functions via CAR (Yamamoto et al., 2004, Cancer Res., 64, 7197-7200). Knockout animals such as CAR knockout mice have been used to examine the relationship between tumorigenic transformation by increased expression of CAR-related drug-metabolizing enzymes and toxicity of a compound like phenobarbital in animals such as mice (Yamamoto et al 2004 Cancer Res 64 7197-7200).

SUMMARY OF THE INVENTION

However, usually, it takes about two years to produce the CAR knockout animals in the case of mice, which lacks rapidity. Further, there is a one in four chances that homo-deficient animals will born from hetero-deficient parents. In the experiment using a large number of homo-deficient animals, for example, test for carcinogenicity of compounds, a lot of effort is required to obtain the animals. Further, in animals such as rats, it is not necessarily the case that the production of knockout animals is easy.

From these circumstances, there is a need to develop a method for inhibiting the CAR gene expression simply and rapidly in a wide range of experimental systems from cultured cells to animal models in each animal species.

The present invention is directed to inhibition of CAR gene expression by RNA interference.

That is, the present invention provides:

1. use of CAR gene as a target gene for inhibiting gene expression by RNA interference;

2. the use of the CAR gene according to the item 1, wherein the CAR gene is used as a target gene for evaluating the toxicity of a chemical substance using as an indicator the level of inhibition of expression of the target gene in a system to which the chemical substance has been administered under the inhibition of the target gene expression by RNA interference;

3. the use of the CAR gene according to the item 1, wherein the CAR gene is used as a target gene for evaluating the toxicity of a chemical substance using as an indicator the level of increase in the expression of a drug-metabolizing enzyme related to the target gene in a system to which the chemical substance has been administered under the inhibition of the target gene expression by RNA interference;

4. the use of the CAR gene according to the item 1, wherein the CAR gene is used as a target gene to evaluate the toxicity of a chemical substance using as an indicator the level of phenotype based on (a) inhibition of expression of the target gene or (b) increase in the expression of a drug-metabolizing enzyme related to the target gene in a system to which the chemical substance has been administered under the inhibition of the target gene expression by RNA interference;

5. a method of inhibiting expression of constitutive active/androstane receptor (CAR) comprising:

administering to a cell an effective amount of a short interfering ribonucleic acid (siRNA) comprising a sense RNA strand and an antisense RNA strand, wherein the sense and the antisense RNA strands form an RNA duplex, and wherein the sense RNA strand comprises a nucleotide sequence identical to a target sequence of about 25 contiguous nucleotides in constitutive active/androstane receptor (CAR) mRNA;

6. the method according to the item 5, wherein the sense RNA strand comprises the sequence of SEQ ID NO: 1, and the antisense strand comprises the sequence of SEQ ID NO: 2;

7. the method according to any one of the items 5 and 6, wherein the cell is a rodent cell and the CAR is a rodent CAR;

8. the method according to the item 7, wherein the rodent is a rat or mouse;

9. the method according to any one of the items 5 to 8, wherein the cell is a cell in vitro or a cell in vivo;

10. the method according to any one of the items 5 to 9, wherein the short interfering ribonucleic acid (siRNA) is administered in conjunction with a delivery carrier;

11. the method according to the item 10, wherein the delivery carrier is selected from the group consisting of lipofectamine, polycations and liposomes;

12. a method for evaluating toxicity of a chemical substance comprising;

(1) inhibiting expression of constitutive active/androstane receptor (CAR) in a cell by RNA interference;

(2) bringing the cell obtained in (1) into contact with a chemical substance; and (3) evaluating the toxicity of the chemical substance to the cell obtained in (2);

13. the method according to the item 12, wherein expression of CAR is inhibited in (1) by the method of any one of the items 5 or 6:

14. the method according to any one of the items 12 and 13, wherein the toxicity of the chemical substance is evaluated in (3) by detecting the level of inhibition of expression of CAR gene in the cell;

15. the method according to any one of the items 12 and 13, wherein the toxicity of the chemical substance is evaluated in (3) by detecting the level of increase in the expression of a drug-metabolizing enzyme related to CAR gene in the cell;

16. the method according to any one of the items 12 and 13, wherein the toxicity of the chemical substance is evaluated in (3) by detecting the level of phenotype based on (a) inhibition of expression of CAR gene or (b) increase in the expression of a drug-metabolizing enzyme related to CAR gene in the cell;

17. the method according to any one of the items 12 to 16, wherein the cell is a rodent cell and the CAR is a rodent CAR;

18. the method according to the item 17, wherein the rodent is a rat or mouse;

19. the method according to any one of the items 12 to 18, wherein the cell is a cell in vitro or a cell in vivo;

20. an isolated short interfering ribonucleic acid (siRNA) comprising a sense RNA strand and an antisense RNA strand, wherein the sense and an antisense RNA strands form an RNA duplex, and wherein the sense RNA strand comprises a nucleotide sequence identical to a target sequence of about 25 contiguous nucleotides in constitutive active/androstane receptor (CAR) mRNA;

21. the short interfering ribonucleic acid (siRNA) according to the item 20, wherein the sense RNA strand comprises the sequence of SEQ ID NO: 1, and the antisense strand comprises the sequence of SEQ ID NO: 2;

22. a composition comprising an effective amount of the short interfering ribonucleic acid (siRNA) of any one of the items 20 and 21 and a delivery carrier, and 23. a hepatocyte comprising the short interfering ribonucleic acid (siRNA) of any one of the items 20 and 21.

According to the present invention, there can be provided siRNAs, compositions and methods for inhibiting the CAR gene expression simply and rapidly, which can be used for evaluating toxicity of a chemical substance.

DETAILED DESCRIPTION OF THE PREFERRED EMBODIMENT

Figure 1:
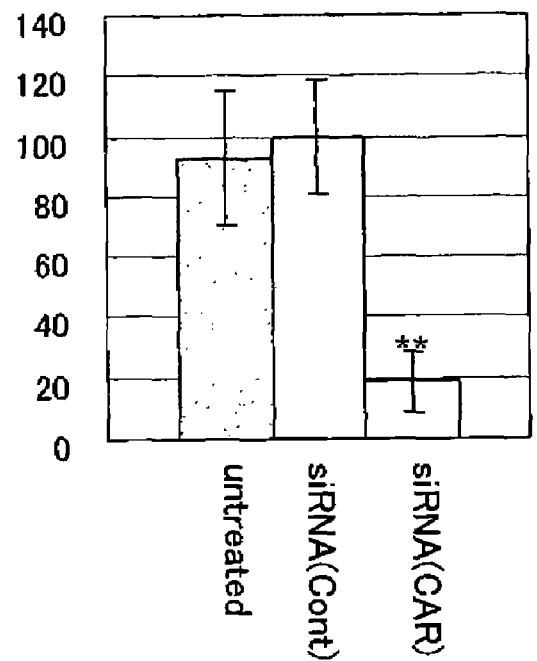
FIG. 1 is a histogram showing relative expression level of CAR mRNA (in %) in each groups in Example 1 (5) based on the expression level in the siRNA(Cont) group as being regarded to be 100%. The each bar represents the average of 2 experiments, and the error bars represent the standard deviation of the mean. ** $P<0.01$

Hereinafter, the use of the CAR gene as a target gene for inhibiting gene expression by RNA interference will be described.

Generally, the specific inhibition of a target gene in RNA interference is performed by allowing to act on the target gene a short double-stranded oligoribonucleotide (hereinafter referred to as ds oligoribonucleotide in some cases) which comprises an overhang of about two nucleotides at least at the terminal of the first strand of the duplex. The ds oligoribonucleotide is known as the short interference RNA (siRNA). The siRNA has a nucleotide sequence matched to a partial sequence of the nucleotide sequence of the CAR gene when the CAR gene is used as the target gene.

For efficient delivery to the liver, it is preferable that the siRNA is modified with a material such as cholesterol. Further, in order to improve preservation stability, it is more preferable that either the sense or antisense strand of the siRNA is chemically modified with 2'-O-methyl or 2'-deoxy.

In the case where siRNA against CAR mRNA is delivered into cultured cells (the term "cultured cells" used herein includes established cell lines or primary cultured cells obtained from, for example, mammals), preferable examples of the delivery method include forward and reverse transfection methods using the calcium chloride method, lipofection method, and electroporation method and the like. Although the lipofection method is more preferable, it is preferable to select an optimal delivery method depending on the type of cultured cell to be introduced.

Examples of the method for delivering siRNA against CAR mRNA to cells in a living body include various methods of administration to target animals. Preferable examples of the method of administration include oral administration, dermal administration, subcutaneous administration, airway administration and transocular administration, intramuscular administration, and intravascular administration. The blood vessels include all arteries and veins in living organisms. Preferable examples thereof include hepatic portal, hepatic artery, tail vein, and jugular vein. In the above methods of administration, siRNA may be administered directly without an external capsule. Preferably, siRNA may be included in or bound to carriers such as liposomes. More preferably, siRNA may be included in or bound to a mixture of liposome and cholesterol, further preferably DMRIE-C Reagent (Invitrogen). When the oral administration is carried out, siRNA may be mixed with foods for feeding organisms.

The effective amount of siRNA to be administered varies depending on the cell types, animal species, administration methods, and the like. The appropriate dosage can vary depending on each condition. For example, as for a single daily administration to living animals, the amount is preferably 0.01 to 1000 mg/kg body weight/day, more preferably 10 mg/kg body weight/day in the case of tail vein administration to mice. In the case of tail vein administration to rats, the amount is preferably 0.01 to 1000 mg/kg body weight/day, more preferably 10 mg/kg body weight/day. The dose per day divided into multiple doses can be given.

When siRNA is administered repeatedly, preferable examples of the hepatic portal administration or hepatic arterial administration may include placement of catheter in the blood vessel, implantation of an osmotic pump containing siRNA, and the like. In the case where surgical intervention is not preferable, tail vein administration, jugular vein administration, and the like are preferred.

In this regard, the dosage interval and the number of repeated-doses can be changed for each condition of the embodiments. For example, in the case of tail vein administration to mice, siRNA is administered at a dose of preferably 0.01 to 1000 mg/kg body weight/day, more preferably 10 mg/kg body weight/day for multiple days. Alternatively, the administration can be performed at least one day apart. For example, in the case of tail vein administration to rats, siRNA is administered at a dose of preferably 0.01 to 1000 mg/kg body weight/day, more preferably 10 mg/kg body weight/day for multiple days. Alternatively, the administration can be performed at least one day apart.

The expression level of the CAR gene, which is the target gene, can be measured by a method for measuring the amount of transcripts of the gene per unit cell mass or a method for measuring the amount of the translated products per unit cell mass.

In order to measure the amount of transcripts of the gene, the amount of mRNA, i.e., transcripts of the gene is measured. The amount of mRNA can be measured by methods such as the quantitative real-time polymerase chain reaction (hereinafter, referred to as quantitative RT-PCR.), the northern hybridization method [J. Sambrook, E. F. Frisch, T. Maniatis work; Molecular Cloning 2nd edition, issued by Cold Spring Harbor Laboratory, 1989], the DNA array method, and the in situ hybridization method.

In order to measure the amount of translated products of the gene, the amount of the protein of the amino acid sequence encoded by the nucleotide sequence of the gene is measured. The amount of protein can be measured by methods including immunological measurement using a specific antibody against the protein such as ELISA, Western blot, RIA, and immunohistochemistry, two-dimensional electrophoresis, and a method using high performance liquid chromatography. In this regard, the specific antibody against the protein can be prepared using the protein as an immunogen in accordance with a conventional method.

The level of inhibition of expression of the CAR gene, i.e., the target gene is determined by comparing the expression level, which is measured by the above-described methods, of the CAR gene in animals receiving the siRNA with the expression level of the CAR gene in the liver of animals such as mammals of the same species, line, sex, and age in week receiving a control siRNA having a nucleotide sequence that is not matched to the nucleotide sequence of the CAR gene of the animal. Although the mammals are not limited, humans, monkeys, marmosets, dogs, rabbits, guinea pigs, rats mice, or the like can be used.

Subsequently, a method for evaluating the toxicity of a chemical substance under the inhibition of the CAR gene expression by RNA interference will be described.

The method for evaluating the toxicity of a chemical substance includes the following three steps:

(1) a first step of inhibiting the CAR expression in cells by RNA interference:

(2) a second step of bringing the cells obtained in the first step into contact with the chemical substance; and (3) a third step of evaluating the toxicity of the chemical substance to the cells obtained in the second step.

Examples of the cells to be used in the first step may include cultured cells or cells in a body of animals. Specific examples thereof may include hypatocytes of mammals. These cells may be used directly, alternatively, cells prepared by separation, fractionation, or immobilization of such cells may be used. Examples of the mammal to obtain cells include rodents such as rats and mice.

In order to inhibit the CAR expression in the cells by RNA interference, the inhibition can be performed by allowing siRNA to act on the CAR gene as described above.

In the second step, when cultured cells are used as cells, a solution containing a chemical substance is added to the culture medium of the cultured cells 24 hours after the treatment of siRNA in the first step. The concentration of the chemical substance of the solution to be added at the time can be changed depending on the combination of cultured cells to be used and the chemical substance. Desirably, the concentration is set to the level that the toxicity of the chemical substance can be evaluated in the third step. Further, it is preferable to newly add the solution of the chemical substance to the culture medium for each replacement of the culture medium.

When cells in the living body of, for example, mammals are used, the chemical substance is administered to the cells after the first step, preferably after multiple days. Examples of the method for administering the chemical substance include oral (gavage or mixed in drinking water or diet), intramuscular, intravenous, subcutaneous, intraperitoneal, and airway routes of administration. In that case, the dose, number of doses, and dosing period may be within the range that does not have a serious impact on general condition of the mammals and organ tissues throughout the body, e.g. below the maximal tolerated dose.

The cells thus obtained from mammals, for example, tissue, cell separated from the tissue, cultured cells of the cells, can be brought into contact with the chemical substance by direct or indirect means.

Specifically, in the second step, when the chemical substance is administered to the cells, for example, of mammals which are obtained in the first step, they are administered orally, subcutaneously, or inhalationally for three days or more in the case where the mammals are adult mammals. In the case of juvenile animals, they are administered orally, subcutaneously, or inhalationally for three days or at least once a day.

The oral administration in the case is carried out using the following procedures.

First, the required amount of the chemical substance is weighed and an appropriate solvent such as corn oil, about 0.25 to 0.5% methylcellulose solution, or the like, is added to the chemical substance, if necessary. Then, a solution or a uniform suspension is prepared, which is used as a dosing solution. When the dosing solution is administered to the mammals, it is preferable to administer at a dose of 5 ml/kg/day or less at least once a day using a syringe, an elastic catheter, and the like.

The subcutaneous administration in the case is carried out using the following procedures.

First, the required amount of the chemical substance is weighed and an appropriate solvent such as corn oil, about 0.25 to 0.5% methylcellulose solution, or the like, is added to the chemical substance, if necessary. Then, a solution or a uniform suspension is prepared, which is used as a dosing solution. When the dosing solution is administered to the mammals, it is preferable to administer at a dose of 4 mL/kg/day or less at least once a day using a syringe, a needle, and the like.

The inhalation administration in the case is carried out using the following procedures.

First, the required amount of the chemical substance is weighed and an appropriate solvent such as corn oil, acetone, etc., is added to the chemical substance, if necessary. Then, a solution or a uniform suspension is prepared, which is used as a dosing solution. Then, the dosing solution is placed in a nebulizer and a suitable exposure chamber is used to allow the mammals to inhale the solution during spontaneous breathing. The inhalation is performed at least once a day (continuously for 4 hours or more per inhalation).

In the third step, the toxicity of the chemical substance to the cells obtained in the second step is evaluated.

The toxicity evaluation can be performed by:

(i) detecting the level of inhibition of expression of the CAR gene in the cells;

(ii) detecting the level of increase in the expression of the CAR gene-related drug-metabolizing enzyme in the cells; or (iii) detecting the level of phenotype based on the inhibition of expression of the CAR gene or the increase in the expression of the car gene-related drug-metabolizing enzyme in the cells.

With reference to the detection (i) described above, the level of inhibition of expression of the CAR gene can be detected by measuring the expression level of the CAR gene.

With reference to the detection (ii) described above, methods generally known in the art may be used in order to detect increase or decrease in the expression level of the CAR gene-related drug-metabolizing enzyme, that is, the level of the increase in the expression of the CAR gene-related drug-metabolizing enzyme, in cultured cells or in cells in the body of mammals which have been brought into contact with the chemical substance. Specific examples thereof include a method for measuring the amount of transcripts or translated products of the gene of the CAR gene-related drug-metabolizing enzyme per unit cell mass.

The term "gene of drug-metabolizing enzyme" which is expressed in the liver means an enzyme gene expressed in liver cells which is involved in metabolic reaction of hormone or drug, which are chemical substances. For example, enzymes involved in the first phase reaction including oxidation, reduction, and hydrolysis in the liver include CYP (Cytochrome P450), ADH (alcohol dehydrogenase), ALDH (aldehyde dehydrogenase), or the like. Enzymes involved in the second phase reaction including conjugation in the liver include UGT (UDP-glucuronosyltraLnsferase), SULT (sulfotransferase), or the like.

In this regard, the CYP includes subtypes of CYP1, CYP2, and CYP3 in rats. Further, CYP2 includes a plurality of subtypes such as CYP2B1. Further, UGT includes subtypes of UGT1A and UGT2B in rats. Furthermore, UGT1A includes a plurality of subtypes such as UGT1A1, UGT1A2, UGT1A3p, UGT1A4, UGT1A5p, UGT1A6, UGT1A7, UGT1A8, UGT1A9, UGT1A10, and UGT1A11. Since respective subtypes have different substrates, subtypes can be selected depending on the intended use. For example, in the safety evaluation of a certain test substance, when its similarity to phenobarbital which is a tumor promoter in rat liver and thyroid is evaluated, it can be determined by comparing the results of animals receiving the test substance with the results of animals receiving phenobarbital using the expression level of CYP2B1, UGT1A1, UGT1A6 induced by phenobarbital or UGT2B1 as indicators. In that case, selection of the subtypes can be readily understand by those skilled in the art who can develop drugs or evaluate the safety of test substances.

Examples of the detection (iii) described above include methods for detecting the increase or decrease in the activity of the CAR gene-related drug-metabolizing enzyme, the increase or decrease in the amount of cell proliferation, the increase or decrease in the amount of apoptosis in cells, the increase or decrease in the amount of production of active oxygen, the increase or decrease in wet weight of the liver, or the increase or decrease in the cell number causing centrilobular hypertrophy of hepatocytes.

Further, methods generally known in the art may be used in order to detect the increase or decrease in the activity of the CAR gene-related drug-metabolizing enzyme in cultured cells or cells in the body of mammals which are contacted with chemical substances.

Specifically, the activity can be determined by bringing a substrate of CAR gene-related drug-metabolizing enzyme into contact with cells and measuring changes in the substrate or its metabolite per unit cell mass. Examples of the method for measuring the amount of substrate or metabolite include a measuring method using reporter gene assay, a measuring method using absorptiometer, a method for measuring the amount of fluorescence, a method for using a radiation marker to measure the radiation dose, a measuring method using immunological measurement using a specific antibody against the substrate or metabolite such as ELISA, Western blot, RIA, and immunohistochemistry, a measuring method using two dimensional electrophoresis, and a measuring method using high performance liquid chromatography.

Further, methods generally known in the art may be used in order to detect the increase or decrease in the amount of cell proliferation in cultured cells or cells in the body of mammals which are contacted with chemical substances.

Specific examples thereof include a method for measuring the increase or decrease in the cell number per unit cell mass and a method for measuring indicators correlated with the increase or decrease in the amount of cell proliferation such as uptake of thymidine or BrdU.

Further, methods generally known in the art may be used in order to detect the increase or decrease in the amount of apoptosis in cultured cells which are contacted with chemical substances or cells in the body of mammals.

Specifically, examples of the method for measuring the apoptosis cell number per unit cell mass include morphological detection at the cell level, histochemical test using an apoptosis-related protein such as Fas as an antigen, TUNEL assay, and cytochrome C release assay (for further information, see "New Experimental Method of Apoptosis, revised 2nd Ed., Yodosha Co., Ltd., issued in 1999").

Further, methods known in the art may be used in order to detect the increase or decrease in the amount of production of active oxygen in cultured cells which are contacted with chemical substances or cells in the body of mammals.

Specifically, the increase or decrease in the amount of production of active oxygen is detected by measurement of $O_2^-$, $H_2O_2$ per unit cell mass, measurement of NO, peroxynitrite, measurement of Lipid peroxide, analysis by Chemiluminescence, ESR analysis using a spin trapping agent, analysis of peroxides by FACS, bioassay for antioxidant activity, or the like (for further information, see "Active Oxygen Experimental Protocol (under the editorial supervision of Naoyuki Taniguchi, Shujunsha Co., Ltd., issued in 1994)").

Further, methods known in the art may be used in order to detect the increase or decrease in wet weight of the liver in cells derived from mammals which are contacted with chemical substances.

Specifically, after measuring the body weight of mammals, and the like immediately prior to dissection, an anesthetic, for example, ether is administered to the mammals. Thereafter, they are sacrificed by collecting the blood from the abdominal aorta. After the sacrifice, the liver is removed and the wet weight is immediately measured using a balance.

Further, methods generally known in the art may be used in order to detect the increase or decrease in the cell number causing centrilobular hypertrophy of hepatocytes in cells in the body of mammals which are contacted with chemical substances.

Specifically, mammals are sacrificed by the above-described method, followed by removing the liver. A portion of the liver is fixed in 10% neutral buffered formalin solution in order to use as cells for histopathological examination and histopathological examination based on optical microscope observations is performed in accordance with an ordinary method. Then, the cell number causing centrilobular hypertrophy of hepatocytes is calculated.

It is expected that the development of therapeutic drug or therapy of pathological conditions and the production of animal models of disease and animal models for safety evaluation will be achieved by controlling CAR gene expressed in the liver in humans using the method of use of the CAR gene as the target gene for inhibiting gene expression by RNA interference. Further, it is considered that the efficacy of drugs administered can be enhanced and further a dose of drugs can be reduced by inhibiting the expression of the CAR gene-related drug-metabolizing enzyme which inhibits the CAR gene expression and is controlled by the gene.

Respective methods, protocols, reagents, apparatuses, and materials according to the present invention described above are intended to illustrate an exemplary embodiment of the present invention. However, the scope of the invention is not limited thereto.

EXAMPLES

Herein below, the present invention will be specifically described with reference to Examples, but it is not to be construed as being limited thereto.

Example 1

Inhibition of CAR in Cultured Cells (1) Preparation of Animals and Cells

Primary cultured hypatocytes were prepared from the liver of a single individual of 10-week-old male Wistar rats. In the preparation of cells, cells were obtained by collagenase liver perfusion and washed with William's culture medium. Thereafter, the cells were inoculated into collagen coated 6 well plates at $3.5 \times 10^5$ cells/well (on day 0). The solution was changed in order to remove dead cells after 3 hours. Examination was carried out using cells of 2 to 4 wells per group (N=2 to 4). The culture medium was changed every day.

(2) RNA Interference siRNA comprising a sequence complementary to mRNA of CAR was produced (sense strand: SEQ ID NO: 1; 5' GCU CAC ACA CUU UGC AGA UAU CAA U 3' and antisense strand: SEQ ID NO: 2: 5' AUU GAU AUC UGC AAA GUG UGU GAG C 3'), and was introduced into cultured cells using Lipofectamine RNAiMax reagent (Invitrogen). With reference to effects of RNA interference, control siRNA (Stealth RNAi Negative Control with Midium GC, manufactured by Invitrogen, Catalog No.: 12935-300) comprising a sequence which is not complementary to any gene sequence was introduced into cultured cells to evaluate as a control group.

Introduction of siRNA into CAR was performed on the day following the inoculation of the cells (on day 1) and treatment was carried out at a final concentration of 100 nM. After 4 hours, the culture medium was replaced with a new culture medium. The cell density was about 50% confluent at the time of introduction.

(3) Preparation of Total RNA

Preparation of RNA was performed 72 hours after the introduction of siRNA (on day 4). The cells were washed with PBS and 1 ml of ISOGEN (manufactured by NIPPON GENE CO., LTD.) was added thereto. The resulting product was pipetted and homogenized by vortexing while it was cooled with ice, which was left at room temperature for 5 minutes. Subsequently, 0.2 ml of chloroform (manufactured by Kanto Chemical Co., Inc.) was added to the resulting product, which was vigorously stirred up and down for 15 seconds and then left at room temperature for 5 minutes. After centrifugation at 4° C. for 15 minutes at 12,000 g, an aqueous layer was collected into a 1.5 ml assist tube (manufactured by Assist). Further, 0.5 ml of 2-propanol (manufactured by Kanto Chemical Co., Inc.) was added to the tube, which was end-over-end mixed and then allowed to stand at room temperature for 10 minutes. After centrifugation at 4° C. for 10 minutes at 12,000 g. the supernatant was removed and a pellet was given. The obtained pellet was washed with 1 ml of 70% ethanol solution. 20 µl of sterile distilled water treated with DEPC was added to the resulting pellet, which was dissolved and a total RNA solution was obtained. The RNA solution was further DNase-treated and purified as directed in the instruction manual using the RNeasy Kit (manufactured by Qiagen).

(4) Preparation of cDNA

The reagent contained in TaqMan Reverse Transcription Regents (manufactured by ABI) (10× Taq Man RT buffer 1 µL, 25 mM $MgCl_2$ 2.2 µL, DeoxyNTPs Mixture 2 µL, Oligo dT 0.5 µL, RNase Inhibitor 0.2 µL, MultiScribe RT 0.25 µL) was mixed with 2.85 µl of sterile distilled water treated with DEPC.

Subsequently, 1 µL of total RNA prepared as described in (3) was added thereto and the obtained mixture was subjected to reverse transcription reaction by incubating at 25° C. for 10 minutes, then at 48° C. for 30 minutes, and then heating at 95° C. for 5 minutes. After the reaction, the reaction mixture was cooled at 4° C., which was used as cDNA solution.

(5) Analysis of CAR Gene Expression Using Quantitative RT-PCR cDNA prepared as described in (4) was used as a template and PCR was performed under the following conditions, then amplified DNAs were quantitated. That is, 25 µl of the reaction solution containing the cDNA 2 µl, Forward primer (SEQ ID NO: 3:5' CCA TCA CCG GCC TTT CC 3') 22.5 pmol, Reverse primer (SEQ ID NO: 4:5' GCT GCA CCA TGA AAG TAT TGA TAT CT 3') 22.5 pmol, probe (SEQ ID NO: 5:5' CCT GGC CCC CGT GTT GCC T 3') 6.25 pmol, and TaqMan Universal Master Mix (manufactured by ABI) 12.5 µl was prepared, which was subjected to incubation at 50° C. for 5 minutes, then at 95° C. for 10 minutes, followed by 40 PCR cycles, 1 cycle being incubation at 95° C. for 15 seconds, and then at 60° C. for 1 minute, using GeneAmp5700 Sequence detection System (manufactured by ABI). The amount of mRNA of CAR gene was quantified from the amount of amplified DNAs.

As a control gene, the amount of mRNA of Glyceraldehyde-3-phosphate dehydrogenase (GAPDH) gene was also quantified in the same manner as described above (Forward primer: SEQ ID NO: 6:5' GCT GCC TTC TCT TGT GAC AAA GT 3', Reverse primer: SEQ ID NO: 7:5' CTC AGC CTT GAC TGT GCC ATT 3', and Probe: SEQ ID NO: 8:5' TGT TCC AGT ATG ATT CTA CCC ACG GCA AG 3'). The ratio of the amount of mRNA of CAR gene to the amount of mRNA of GAPDH gene was calculated, which was used as the CAR gene expression level. In the untreated group, the group treated with siRNA (Cont), and the group receiving siRNA(CAR), the CAR gene expression level in cells was respectively determined. As a result, the CAR gene expression level in the group receiving siRNA(CAR) was reduced to about 30% as compared to the CAR expression level in the group treated with siRNA(Cont) (see FIG. 1).

Example 2

Inhibition of CAR Gene in the Liver of Rats by a Single Tail Vein Administration of CAR siRNA (1) Preparation for Mammalian Subjects Four(4)-week-old male Crl:CD (SD) rats (purchased from CHARLES RIVER LABORATORIES JAPAN, INC.) were quarantined for one week and then the 5-week-old rats were subjected to experiments.

(2) Preparation of Dosing Solution Containing siRNA(CAR) Using CAR as Target Gene or Control siRNA(Cont)

siRNA(CAR) using CAR as a target gene (sense strand: SEQ ID NO: 1; 5' GCU CAC ACA CUU UGC AGA UAU CAA U 3' and antisense strand: SEQ ID NO: 2; 5' AUU GAU AUC UGC AAA GUG UGU GAG C 3') (manufactured by Invitrogen) was dissolved in Ringer's solution at a concentration of 0.8 mg/mL, which was mixed with an equivalent volume of DMRIE-C reagent (Invitrogen). Further, the control siRNA(Cont) (Stealth RNAi Negative Control with Midium GC, manufactured by Invitrogen, Catalog No.: 12935-300) was dissolved in Ringer's solution at a concentration of 0.8 mg/mL, which was mixed with an equivalent volume of DMRIE-C reagent.

(3) Administration to Mammalian Subjects

The weight of the mammalian subjects prepared in (1) was measured for each individual using a balance, and then the dosing solution containing siRNA(CAR) prepared in (2) was administered via the tail vein by injection at a dose of 10 mg/kg/day in a volume of 12 mL/mg/day once daily (hereinafter referred to as mammals receiving siRNA(CAR)). As for control mammals, a dosing solution containing control siRNA(Cont) was administered in place of the dosing solution containing siRNA(CAR) in the same manner as the case of the mammals receiving siRNA(CAR) (hereinafter referred to as mammals receiving control siRNA(Cont)). Further, in order to grasp the effects caused by these treatments, animals which received nothing were determined (hereinafter referred to as untreated animals). In each case, three to five mammalian subjects were used.

(4) Observation, Measurement, and Examination to Identify Toxicity

With reference to all of the animals administered, viability test, measurement of body weight (just before the administration and at the time of dissection), necropsy at the time of dissection, blood biochemical test (for example, ALT, AST, LDH, gamma-GTP, etc.), measurement of liver weight, and histopathological examination of the liver were performed in accordance with an ordinary method in order to grasp the toxicity by administration. Consequently, no significant toxicity was observed in mammals receiving control siRNA (Cont).

(5) Collection and Storage of Test Samples

After measuring the body weight immediately prior to dissection, an appropriate anesthetic, for example, ether was administered to mammals being dissected. Thereafter, they were sacrificed by collecting the blood from the abdominal aorta. After the sacrifice, organs throughout the body were necropsied (gross pathological observation). Then, the liver was removed and the wet weight was immediately measured using a balance. After measuring the weight, the liver was isolated and a portion of the liver was placed into the RNA later (manufactured by Ambion) to use as the liver tissue for RNA expression analysis, which was stored at 4° C. until the analysis. Alternatively, another portion of the liver was freezed with liquid nitrogen to use as the liver tissue for protein analysis, which was then stored at −80° C. until the analysis. Further, histopathological examination based on optical microscope observations was performed in accordance with an ordinary method. Further, the obtained blood was heparinized and the plasma was preparatively isolated, followed by performing the blood biochemical test of the plasma.

(6) Preparation of Total RNA

One(1) ml of ISOGEN (manufactured by NIPPON GENE Co., LTD.) was added based on 10 to 50 mg (wet weight) of the liver tissue stored as described in (5). The resulting product was homogenized by Polytron homogenizer while it was cooled with ice, which was left at room temperature for 5 minutes. Subsequently, 0.2 ml of chloroform (manufactured by Kanto Chemical Co., Inc.) was added to the resulting product, which was vigorously stirred up and down for 15 seconds and then left at room temperature for 5 minutes. After centrifugation at 4° C. for 15 minutes at 12,000 g, an aqueous layer was collected into a 1.5 ml assist tube (manufactured by Assist). Further, 0.5 ml of 2-propanol (manufactured by Kanto Chemical Co., Inc.) was added to the tube, which was end-over-end mixed and then allowed to stand at room temperature for 10 minutes. After centrifugation at 4° C. for 10 minutes at 12,000 g, the supernatant was removed and a pellet was given. The obtained pellet was washed with 1 ml of 70% ethanol solution. 20 µl of sterile distilled water treated with DEPC was added to the resulting pellet, which was dissolved and a total RNA solution was obtained. The total RNA solution was further DNase-treated and purified as directed in the instruction manual using the RNeasy Kit (manufactured by Qiagen).

(7) Preparation of cDNA

The reagent contained in TaqMan Reverse Transcription Regents (manufactured by ABI) (10× Taq Man RT buffer 1 µL, 25 mM $MgCl_2$ 2.2 µL, DeoxyNTPs Mixture 2 µL, Oligo dT 0.5 µL, RNase Inhibitor 0.2 µL, MultiScribe RT 0.25 µL) was mixed with 2.85 µl of sterile distilled water treated with DEPC.

Subsequently, 1 µL of total RNA prepared as described in (6) was added thereto and the obtained mixture was subjected to reverse transcription reaction by incubating at 25° C. for 10 minutes, then at 48° C. for 30 minutes, and then heating at 95° C. for 5 minutes. After the reaction, the reaction mixture was cooled at 4° C., which was used as cDNA solution.

(8) Analysis of CAR Gene Expression Using Quantitative RT-PCR cDNA prepared as described in (7) was used as a template and PCR was performed under the following conditions, then amplified DNAs were quantitated. That is, 25 µl of the reaction solution containing the cDNA 2 µl, Forward primer (SEQ ID NO: 3: 5' CCA TCA CCG GCC TTT CC 3') 22.5 pmol, Reverse primer (SEQ ID NO: 4: 5' GCT GCA CCA TGA AA GTA TTG ATA TCT 3') 22.5 pmol, probe (SEQ ID NO: 5: 5' CCT GGC CCC CGT GTT GCC T 3') 6.25 pmol, and TaqMan Universal Master Mix (manufactured by ABI) 12.5 µl was prepared, which was subjected to incubation at 50° C. for 5 minutes, then at 95° C. for 10 minutes, followed by 40 PCR cycles, 1 cycle being incubation at 95° C. for 15 seconds, and then at 60° C. for 1 minute, using GeneAmp5700 Sequence detection System (manufactured by ABI). The amount of mRNA of CAR gene was quantified from the amount of amplified DNAs.

Figure 2:
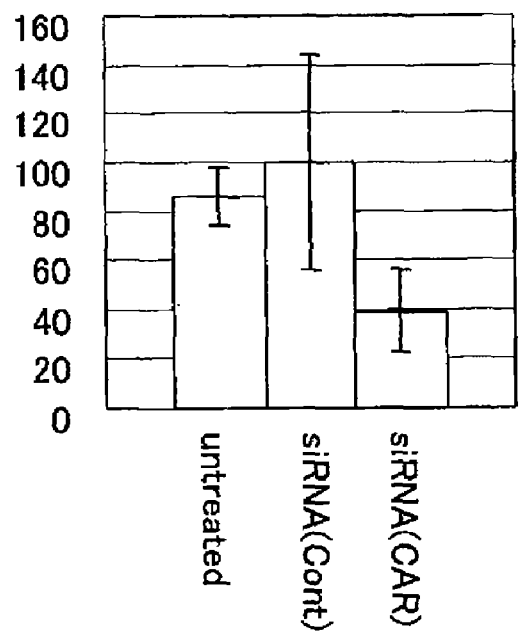
FIG. 2 is a histogram showing relative expression level of CAR mRNA (in %) in each groups in Example 2 (8) based on the expression level in the siRNA(Cont) group as being regarded to be 100%. The each bars represent the average of 3 experiments, and the error bar represent the standard deviation of the mean.

Alternatively, as a control gene, the amount of mRNA of Glyceraldehyde-3-phosphate dehydrogenase (GAPDH) gene was quantified in the same manner as described above (Forward primer: SEQ ID NO: 6: 5' GCT GCC TTC TCT TGT GAC AAA GT 3', Reverse primer: SEQ ID NO: 7: 5' CTC AGC CTT GAC TGT GCC ATT 3', and Probe: SEQ ID NO: 8: 5' TGT TCC AGT ATG ATT CTA CCC ACG GCA AG 3'). The ratio of the amount of mRNA of CAR gene to the amount of mRNA of GAPDH gene was calculated, which was used as the CAR gene expression level. In the untreated animal group, the mammal group receiving siRNA(Cont), and the mammal group receiving siRNA(CAR), the CAR gene expression level in the liver tissue was respectively determined for each individual. As a result, as compared to the CAR gene expression level in the liver tissue of the mammal group receiving siRNA(Cont), the CAR gene expression level in the liver tissue of the mammal group receiving siRNA (CAR) was reduced up to 40% (FIG. 2) one day following the administration (the day after administration).

Example 3

Analysis of Expression of CAR Using Protein Expression Analysis

The liver tissue for protein analysis stored by the method described in (5) of Example 2 was homogenized in 20 mL of buffer for grinding (PBS solution containing 10 mg/mL of leupeptin, 1 mg/mL of pepstatin, and 200 μM of PMSF as protease inhibitors) using a homogenizer (manufactured by Polytron). A portion of the sample was aliquoted into a 1.5 mL tube (manufactured by Eppendorf Co., Ltd.), which was centrifuged at 15,000 rpm at 4° C. for 30 minutes and the resulting supernatant was used for protein analysis. The concentration of proteins contained was measured at an absorbance of 595 nm with an absorptiometer using the Protein assay reagent (manufactured by Bio-Rad Laboratories, Inc.). In Western blotting, 50 μg of protein sample was added to the precast gel (manufactured by Bio-Rad Laboratories, Inc.), which was subjected to electrophoresis under electrophoresis conditions (120 V, 30 mA, 80 min). Transfer was performed under electrophoresis conditions (270 V, 350 mA, 60 min) using Hybond membrane (manufactured by GE Healthcare). In the treatment of primary antibody, blocking was carried out with TBST solution containing 5% skim milk for 1 hour. Then, the membrane was washed with TBST solution several times, which was treated with TBST solution containing anti-CAR polyclonal antibody at a 1:1000 dilution (manufactured by Santa Cruz Biotechnology, Inc.) at 4° C. for about 12 hours. In the treatment of secondary antibody, the membrane was washed with TBST solution several times, which was treated with TBST solution containing anti-rabbit IgG antibody at a 1:1000 dilution (manufactured by Santa Cruz Biotechnology, Inc.) at room temperature for about 2 hours. In detection of antibodies, bands were visualized using Chemi-Lumi One reagent (manufactured by Nacalai Tesque, Inc.) and bands of CAR in the vicinity of 46 KD were measured with a Lumino image analyzer (manufactured by Fuji Photo Film Co., Ltd.). Subsequently, in order to measure β-actin as a control of endogenous protein, the membrane was treated with 20 mL of stripping buffer (manufactured by PIERCE), from which antibodies were removed. Thereafter, the same steps as described above were carried out using anti-β actin antibody (manufactured by Santa Cruz Biotechnology, Inc.) as the primary antibody. The ratio of the band of CAR to the band of β-actin was calculated, which was used as the CAR protein expression level. In the untreated animal group, the mammal group receiving siRNA(Cont), and the mammal group receiving siRNA(CAR), the CAR protein expression level in the liver tissue was respectively determined for each individual. As a result, as compared to the CAR protein expression level in the liver tissue of the mammal group receiving siRNA(Cont), the CAR protein expression level in the liver tissue of the mammal group receiving siRNA(CAR) was reduced up to 50% three days following the administration.

Example 4

Inhibition of CAR Gene Expression in Mice

Figure 3:
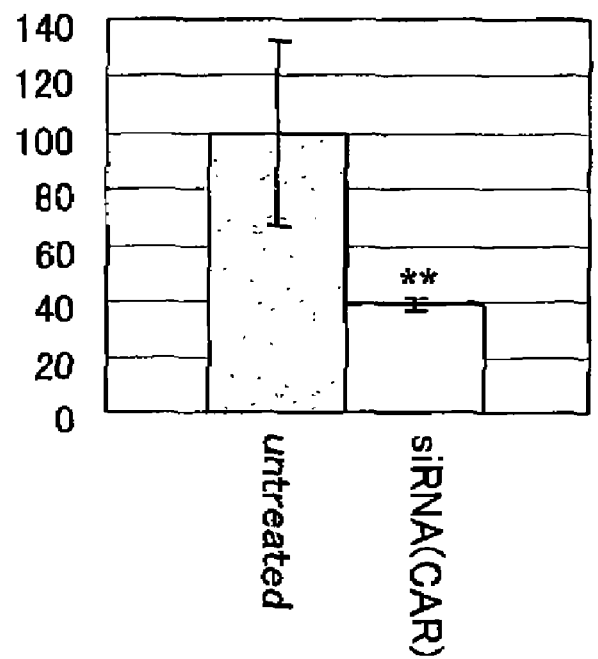
FIG. 3 is a histogram showing relative expression level of CAR mRNA (in %) in each groups in Example 4 based on the expression level in the PB(+)siRNA(Cont) group as being regarded to be 100%. The each bar represents the average of 4 experiments, and the error bars represent the standard deviation of the mean.  $P<0.01$

Five(S)-week-old male Crj:CD-1 mice (purchased from CHARLES RIVER LABORATORIES JAPAN, INC.) were quarantined for one week and then the 5-week-old mice were subjected to experiments. In the same manner as described in Example 2 (2), siRNA(CAR) using CAR as a target gene was produced (sense strand: SEQ ID NO: 1; 5' GCU CAC ACA CUU UGC AGA UAU CAA U 3', and antisense strand: SEQ ID NO: 2; 5' AUU GAU AUC UGC AAA GUG UGU GAG C 3'). The dosing solution containing the siRNA(CAR) was subjected to processes described in (3) to (7) of Example 2 and cDNA was prepared. PCR of CAR gene was performed and as a control gene, PCR of Glyceraldehyde-3-phosphate dehydrogenase (GAPDH) gene was performed by the process described in (8) of Example 2 using the prepared cDNA as a template. The amplified DNAs were quantitated. In this regard, as for primers and probes when quantitative RT-PCR was carried out, primers and probes for mouse CAR gene (Forward primer: SEQ ID NO: 9: 5' GCA TCA CCG GCC TTT CC 3', Reverse primer: SEQ ID NO: 10: 5' CCA TAA ACG TGT TGA TAT CTG CAA A 3', and probe: SEQ ID NO: 11: 5' CCC CGT GTT GCC TCT GCT CAC AC 3') and primers and probes for mouse GAPDH gene (Forward primer: SEQ ID NO: 12: 5' TGT GTC CGT CGT GGA TCT GA 3', Reverse primer: SEQ ID NO: 13: 5' CCT GCT TCA CCA CCT TCT TGA 3', and probe: SEQ ID NO: 14: 5' CCG CCT GGA GAA ACC TGC CAA GTA TG 3') were used. The ratio of the amount of mRNA of CAR gene to the amount of mRNA of GAPDH gene was calculated, which was used as the CAR gene expression level. In the untreated animal group and the mammal group receiving siRNA(CAR), the CAR gene expression level in the liver tissue was respectively determined for each individual. As a result, as compared to the CAR gene expression level in the liver tissue of the untreated animal group, the CAR gene expression level in the liver tissue of the mammal group receiving siRNA (CAR) was reduced up to 40% (FIG. 3) one day following the administration (the day after administration).

Example 5

Toxicity Evaluation of Phenobarbital (PB) Using Cultured Cells (1) Treatment with Compound Twenty four (24) hours after rat primary hepatocyte cultured cells were treated with siRNA(CAR) or control siRNA (Cont) by the methods described in (1) to (2) of Example 1, a PB solution was added to the culture medium at a final concentration of 50 nM (on day 2). The compound was newly added when the culture medium was replaced every day. A group (untreated group) to which PB was not added was prepred as a control.

(2) Analysis of Expression of CAR Gene and CYP2B1 Enzyme Gene Using Quantitative RT-PCR cDNA prepared by the methods described in (1) to (4) of Example 1 from the cells obtained in (1) of Example 5 was used as a template, PCR was performed in the same manner as described in (5) of Example 1 under the following conditions, and then the amount of DNA for each amplified gene was quantitated. That is, 25 µl of the reaction solution containing the cDNA 2 µl, Forward primer against CAR gene (SEQ ID NO: 3: 5' CCA TCA CCG GCC TTT CC 3') 22.5 pmol, Reverse primer (SEQ ID NO: 4: 5' GCT GCA CCA TGA AA GTA TTG ATA TCT 3') 22.5 pmol, probe (SEQ ID NO: 5: 5' CCT GGC CCC CGT GTT GCC T 3') 6.25 pmol, and TaqMan Universal Master Mix (manufactured by ABI) 12.5 µl was prepared, which was subjected to incubation at 95° C. for 5 minutes, then at 50° C. for 10 minutes, followed by 40 PCR cycles, 1 cycle being incubation at 95° C. for 15 seconds, and then at 60° C. for 1 minute, using GeneAmp5700 Sequence detection System (manufactured by ABI). The amount of mRNA of CAR gene was quantified from the amount of amplified DNAs.

With reference to CYP2B1 gene expression, 25 µl of the reaction solution containing Forward primer against CYP2B1 (SEQ ID NO: 15: 5' GCT CAA GTA CCC CCA TGT CG 3') 45 pmol, Reverse primer (SEQ ID NO: 16:5' ATC AGT GTA TGG CAT TTT ACT GCG G 3') 45 pmol, and Power SYBR Green PCR Master Mix (manufactured by ABI) 12.5 µl was prepared, which was subjected to incubation at 95° C. for 10 minutes followed by 40 PCR cycles, 1 cycle being incubation at 95° C. for 30 seconds, and then at 60° C. for 30 seconds, and further at 72° C. for 45 seconds, using GeneAmp5700 Sequence detection System (manufactured by ABI). The amount of mRNA of CYP2B1 gene was quantified from the amount of amplified DNAs.

Figure 4:
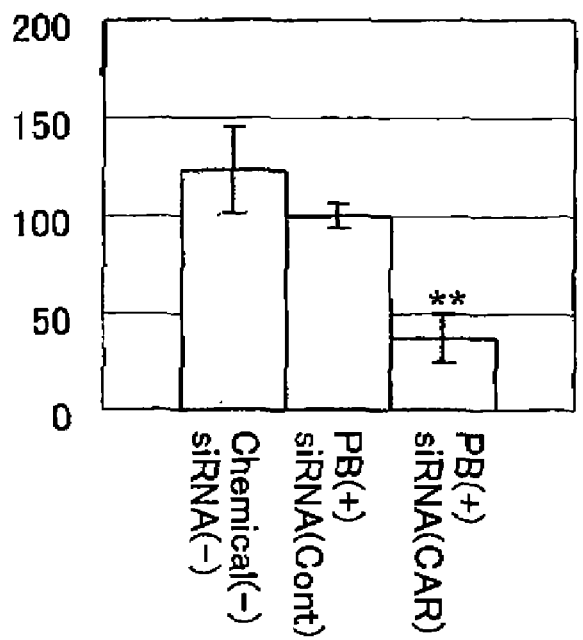
FIG. 4 is a histogram showing relative expression level of CAR mRNA (in %) in each groups in Example 5 (2) based on the expression level in the PB(+)siRNA(Cont) group as being regarded to be 100%. The each bar represents the average of 4 experiments, and the error bars represent the standard deviation of the mean.  $P<0.01$

Alternatively, as a control gene, the amount of mRNA of Glyceraldehyde-3-phosphate dehydrogenase (GAPDH) gene was quantified in the same manner as described above (Forward primer: SEQ ID NO: 6: 5' GCT GCC TTC TCT TGT GAC AAA GT 3', Reverse primer: SEQ ID NO: 7: 5' CTC AGC CTT GAC TGT GCC ATT 3', and Probe: SEQ ID NO: 8: 5' TGT TCC AGT ATG ATT CTA CCC ACG GCA AG 3'). The ratio of the amount of mRNA of CAR gene to the amount of mRNA of GAPDH gene was calculated, which was used as expression levels of CAR genes. The CAR gene expression level in untreated cells, cells treated with control siRNA (Cont), and cells treated with siRNA(CAR) was respectively determined. The ratio of the amount of mRNA of CYP2B1 gene to the amount of mRNA of GAPDH gene was calculated, which was used as expression levels of CYP2B1 genes. The CYP2B1 gene expression level in untreated cells, cells treated with control siRNA(Cont), and cells treated with siRNA(CAR) was respectively determined. As a result, the CAR gene expression level in the cells treated with PB and siRNA (CAR) was reduced to about 40% as compared to the CAR gene expression level in the cells treated with PB and control siRNA(Cont) (see FIG. 4).

Figure 5:
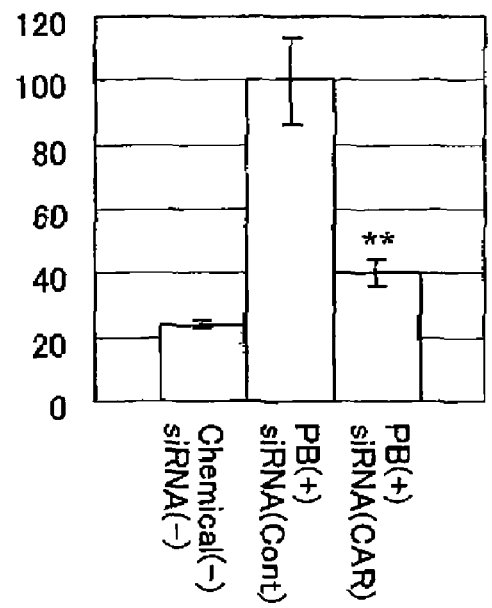
FIG. 5 is a histogram showing relative expression level of CYP2B1 mRNA (in %) in each groups in Example 5 (3) based on the expression level in the PB(+)siRNA(Cont) group as being regarded to be 100%. The each bar represents the average of 4 experiments, and the error bars represent the standard deviation of the mean.  $P<0.01$
Figure 6:
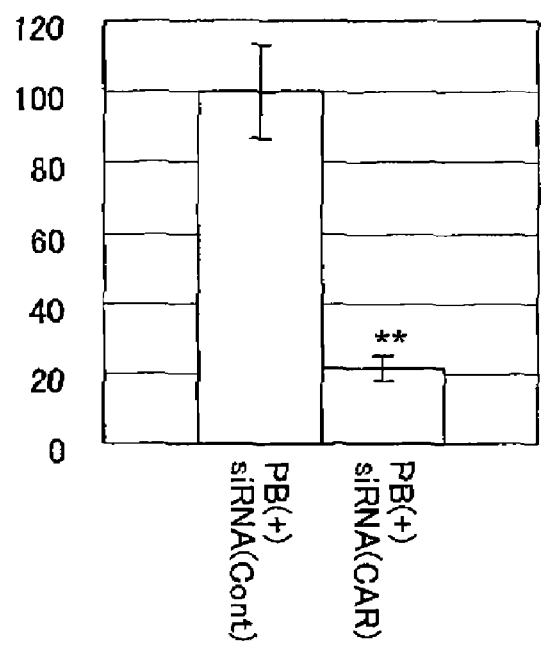
FIG. 6 is a histogram showing relative induced expression level of CYP2B1 mRNA (in %) in each groups in Example 5 (3) based on the induced expression level in the PB(+)siRNA (Cont) group as being regarded to be 100%, where the expression level of the untreated group, which is a steady-state expression level, is subtracted from the expression level of the each groups to determine the induced expression level. The each bar represents the average of 4 experiments, and the error bars represent the standard deviation of the mean.  $P<0.01$

(3) Verification of Toxicity Evaluation System of Phenobarbital (PB) Using Expression of CAR Gene-Related Drug-Metabolizing Enzyme (CYP2B1) as an Indicator In cells treated with PB and control siRNA(Cont), CYP2B1 mRNA expression was increased about fivefold compared to cells untreated with PB (FIG. 5). On the other hand, in cells which inhibited CAR, CYP2B1 expression by PB treatment was increased about twofold compared to cells untreated with compound, and thus a significant reduction was observed (FIG. 5). The amount of change in the induced part obtained by subtracting the CYP2B1 expression in the cells untreated with compound was reduced to 80% or more by inhibition of CAR (FIG. 6). This shows that induction of CYP2B1 expression by PB treatment is achieved via CAR.

Example 6

Verification of Toxicity Evaluation System Using CYP2B Dependent Prod (pentoxyresorufin O-depentylation Activity) as an Indicator In cells treated in the same manner as described in (1) of Example 5, the culture medium is washed with William's culture medium twice 72 hours after the introduction of siRNA (on day 4). Then, the culture medium is replaced with 2 mL of William's culture medium containing 7 µM of 7-pentoxyresorufin and 7 µM of dicumarol. The culture medium is incubated at 37° C. for 4 hours, and then the culture medium is recovered. The cells are mixed with 1000 U of β-glucronidase (bovine liver-derived) and 50 mM of sodium acetate solution (pH 5), which is left at 37° C. for 3 hours. Measurement of pentoxyresorufin O-depentylation activity is performed by measuring the amount of fluorescence per unit solution. Further, the measurement is carried out at an excitation wavelength of 530 nm and a fluorescence wavelength of 585 nm using a fluorophotometer (F-4010, manufactured by Hitachi). In evaluation of the results, the total amount of protein in the cells in which the substrate was treated is measured by the Protein assay kit (Bio-Rad) and the production amount of resorufin per unit protein (amount of pentoxyresorufin O-depentylation) is calculated on the basis of the calibration curve of resorufin. With reference to untreated cells, cells treated with PB and control siRNA (Cont), and cells treated with PB and siRNA (CAR), respective production amounts are determined. As a result, pentoxyresorufin O-depentylation activity is enhanced by PB and control siRNA (Cont) treatment as compared to the case of the untreated cells. On the other hand, activity of the cells treated with PB and siRNA (CAR) is the same as that of the untreated cells. This shows that the induction of pentoxyresorufin O-depentylation activity by PB treatment is achieved via CAR.

Example 7

Verification of Evaluation System Using Cell Proliferation as an Indicator

In cells treated in the same manner as described in (1) of Example 5, 200 µL/well of a BrdU-labeled solution is added to the culture medium using the cell proliferation ELISA, BrdU chemiluminescence kit (manufactured by Roche Diagnostics) 48 hours after the introduction of siRNA (on day 3) and then cultured at 37° C. for 24 hours. The solution is sucked 72 hours after the introduction of siRNA (on day 4) and 2 mL of FixDenat is added thereto, which is left at room temperature for 30 minutes. Thereafter, FixDenat is removed and anti-BrdU-POD was added thereto, which is left at room temperature for 90 minutes. The solution is removed and the remained cells are washed with PBS 3 times. Thereafter, the cells are peeled from the plate by trypsin treatment. 2 mL of substrate solution is added to the cells and then 200 μL of the cell culture solution is aliquoted into a 96-well plate. The bottom of the transparent plate is sealed with a black adhesive foil, which is left on a shaker for 3 minutes, followed by measuring with a microplate luminometer (MicroLumat Plus LB96V, manufactured by Berthold). In the evaluation, the amounts of fluorescence as to untreated cells, cells treated with PB and control siRNA (Cont), and cells treated with PB and siRNA (CAR) are respectively measured. As a result, the uptake of BrdU is enhanced by PB and control siRNA (Cont) treatment as compared to the case of the untreated cells. On the other hand, the uptake of BrdU into the cells treated with PB and siRNA (CAR) is the same as that of the untreated cells. This shows that the enhancement of cell proliferation by PB treatment is achieved via CAR.

Example 8

Verification of Evaluation System Using Cell Apoptosis as an Indicator

In cells treated in the same manner as described in (1) of Example 5, apoptotic cells are stained by the TUNEL assay 72 hours after the introduction of siRNA (on day 4). Then, the total number per well is counted. When apoptosis proceeds, DNA degradation is caused. In Tunel method, FITC-labeled dUTP is bound to the DNA fragment by using TdT (terminal deoxynucleotidyl transferase). When the labeled fragment is observed with a fluorescence microscope, apoptotic cells generate fluorescence. The present experiments are performed using In situ cell death detection kit and Fluorescein (manufactured by Roche Diagnostics).

In the evaluation, fluorescence values as to untreated cells, cells treated with PB and control siRNA (Cont), and cells treated with PB and siRNA (CAR) are respectively determined and the resulting values are used as the amount of apoptosis. As a result, the amount of cell apoptosis is decreased by PB and control siRNA (Cont) treatment as compared to the case of the untreated cells. On the other hand, the uptake of BrdU into the cells treated with PB and siRNA (CAR) is the same as that of the untreated cells. This shows that the decrease of apoptosis by PB treatment is achieved via CAR.

Example 9

Verification of Evaluation System Using Active Oxygen Production as an Indicator In cells treated in the same manner as described in (1) of Example 5, 100 μL of the culture supernatant is aliquoted into a 96-well plate 72 hours after the introduction of siRNA (on day 4), and then 100 μL of Luminol solution is added thereto.

The bottom of the transparent plate is sealed with a black adhesive foil, which is left on a shaker for 3 minutes, followed by measuring with a microplate luminometer (SpectraMaxL, manufactured by Molecular Devices Corporation).

In the evaluation, the amounts of fluorescence as to untreated cells, cells treated with PB and control siRNA (Cont), and cells treated with PB and siRNA (CAR) are respectively measured. As a result, the amount of active oxygen is increased by PB and control siRNA (Cont) treatment as compared to the case of the untreated cells. On the other hand, the amount of active oxygen in the cells treated with PB and siRNA (CAR) is the same as that in the untreated cells. This shows that the increase in the amount of active oxygen by PB treatment is achieved via CAR.

Example 10

Verification of Evaluation System Using Liver Weight as an Indicator

The wet weight of the liver in the rats to which siRNA (CAR) or control siRNA (Cont) was administered by the methods described in (1) to (3) of Example 2 is measured by the method described in (5) of Example 2. As a result, the liver weight is increased in the group treated with PB and control siRNA (Cont) as compared to the case of the untreated animal group. On the other hand, the liver weight in the group receiving PB and siRNA (CAR) is the same as that in the untreated group. This shows that the increase in the liver weight by PB treatment is achieved via CAR.

Example 11

Verification of Evaluation System Using the Cell Number Causing Centrilobular Cell Hypertrophy as an Indicator Histopathological examination of the liver in the rats to which siRNA (CAR) or control siRNA (Cont) was administered by the methods described in (1) to (3) of Example 2 is performed by the method described in (5) of Example 2. As a result, centrilobular cell hypertrophy is increased in the group treated with PB and control siRNA (Cont) as compared to the case of the untreated animal group. On the other hand, the centrilobular cell hypertrophy in the group receiving PB and siRNA (CAR) is the same as that in the untreated group. This shows that the increase in the centrilobular cell hypertrophy by PB treatment is achieved via CAR.

What is claimed is:

1. A method of inhibiting expression of constitutive active/androstane receptor (CAR) comprising:

administering to a cell an effective amount of a short interfering ribonucleic acid (siRNA) comprising a sense RNA strand and an antisense RNA strand, wherein the sense and the antisense RNA strands form an RNA duplex, the sense RNA strand comprises a nucleotide sequence identical to a target sequence of about 25 contiguous nucleotides in constitutive active/androstane receptor (CAR) mRNA, the sense RNA strand comprises the sequence of SEQ ID NO: 1, and the antisense RNA strand comprises the sequence of SEQ ID NO: 2.

2. The method according to claim 1, wherein the cell is a rodent cell and the CAR is a rodent CAR.

3. The method according to claim 2, wherein the rodent is a rat or mouse.

4. The method according to claim 1, wherein the cell is a cell in vitro or a cell in vivo.

5. The method according to claim 1, wherein the short interfering ribonucleic acid (siRNA) is administered in conjunction with a delivery carrier.

6. The method according to claim 5, wherein the delivery carrier is selected from the group consisting of lipofectamine, polycations and liposomes.

7. A method for evaluating toxicity of a chemical substance comprising:

(1) inhibiting expression of constitutive active/androstane receptor (CAR) in a cell by RNA interference;

(2) bringing the cell obtained in (1) into contact with a chemical substance; and (3) evaluating the toxicity of the chemical substance to the cell obtained in (2)

wherein in (1), the expression of CAR is inhibited by administering to the cell an effective amount of a short interfering ribonucleic acid (siRNA) comprising a sense RNA strand and an antisense RNA strand, wherein the sense and the antisense RNA strands form an RNA duplex, the sense RNA strand comprises a nucleotide sequence identical to a target sequence of about 25 contiguous nucleotides in constitutive active/androstane receptor (CAR) mRNA, the sense RNA strand comprises the sequence of SEQ ID NO: 1, and the antisense RNA strand comprises the sequence of SEQ ID NO: 2.

8. The method according to claim 7, wherein the toxicity of the chemical substance is evaluated in (3) by detecting the level of inhibition of expression of CAR gene in the cell.

9. The method according to claim 7, wherein the toxicity of the chemical substance is evaluated in (3) by detecting the level of increase in the expression of a drug-metabolizing enzyme related to CAR gene in the cell.

10. The method according to claim 7, wherein the toxicity of the chemical substance is evaluated in (3) by detecting the level of phenotype based on (a) inhibition of expression of CAR gene or (b) increase in the expression of a drug-metabolizing enzyme related to CAR gene in the cell.

11. The method according to claim 7, wherein the cell is a rodent cell and the CAR is a rodent CAR.

12. The method according to claim 11, wherein the rodent is a rat or mouse.

13. The method according to claim 7, wherein the cell is a cell in vitro or a cell in vivo.

14. An isolated short interfering ribonucleic acid (siRNA) comprising a sense RNA strand and an antisense RNA strand, wherein the sense and an antisense RNA strands form an RNA duplex, the sense RNA strand comprises a nucleotide sequence identical to a target sequence of about 25 contiguous nucleotides in constitutive active/androstane receptor (CAR) mRNA, the sense RNA strand comprises the sequence of SEQ ID NO: 1, and the antisense strand comprises the sequence of SEQ ID NO: 2.

15. A composition comprising an effective amount of the short interfering ribonucleic acid (siRNA) of claim 14 and a delivery carrier.

16. An isolated non-human mammalian hepatocyte comprising the short interfering ribonucleic acid (siRNA) of claim 14.

* * * * *

SEQUENCE LISTING

<160> NUMBER OF SEQ ID NOS: 16

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence:Designed oligonucleotide for RNA interference

<400> SEQUENCE: 1
gcucacacac uuugcagaua ucaau                                    25

<210> SEQ ID NO 2
<211> LENGTH: 25
<212> TYPE: RNA
<213> ORGANISM: Artificial Sequence
<220> FEATURE:
<223> OTHER INFORMATION: Description of Artificial Sequence:Designed
      oligonucleotide for RNA interference

<400> SEQUENCE: 2
auugauaucu gcaaagugug ugagc                                    25

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 3
ccatcaccgg cctttcc                                             17

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 4
gctgcaccat gaaagtattg atatct                                   26

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:Designed
      oligonucleotide probe for PCR

<400> SEQUENCE: 5
cctggccccc gtgttgcct                                           19

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 6
gctgccttct cttgtgacaa agt                                      23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 7
ctcagccttg actgtgccat t                                              21

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:Designed
      oligonucleotide probe for PCR

<400> SEQUENCE: 8
tgttccagta tgattctacc cacggcaag                                      29

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 9
gcatcaccgg cctttcc                                                   17

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 10
ccataaacgt gttgatatct gcaaa                                          25

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:Designed
      oligonucleotide probe for PCR

<400> SEQUENCE: 11
ccccgtgttg cctctgctca cac                                            23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 12
tgtgtccgtc gtggatctga                                                20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:Designed
      oligonucleotide primer for PCR -continued

```
<400> SEQUENCE: 13
cctgcttcac caccttcttg a                                              21

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:Designed
      oligonucleotide probe for PCR

<400> SEQUENCE: 14
ccgcctggag aaacctgcca agtatg                                         26

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 15
gctcaagtac ccccatgtcg                                                20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 16
atcagtgtat ggcattttac tgcgg                                          25
```